United States Patent [19]
Walters et al.

[11] Patent Number: 5,961,495
[45] Date of Patent: Oct. 5, 1999

[54] MEDICATION DELIVERY PEN HAVING A PRIMING MECHANISM

[75] Inventors: Daniel A. Walters, Rockaway Twp., N.J.; Marco Carroll Perry, Brooklyn, N.Y.; Hyung J. Lee, Rockville, Md.

[73] Assignee: Becton, Dickinson and Company, Franklin Lakes, N.J.

[21] Appl. No.: 09/026,585

[22] Filed: Feb. 20, 1998

[51] Int. Cl.[6] .................................................. A61M 5/00
[52] U.S. Cl. ..................... 604/208; 604/209; 604/211; 604/232; 604/111; 604/210
[58] Field of Search .................... 604/122, 124, 604/125, 131, 152, 111, 181, 187, 207, 208, 209, 210, 211, 232; 222/43, 309, 390

[56] References Cited

U.S. PATENT DOCUMENTS

| 4,865,591 | 9/1989 | Sams | 604/208 |
|---|---|---|---|
| 5,114,408 | 5/1992 | Gabriel et al. | 604/232 |
| 5,514,097 | 5/1996 | Knauer | 604/187 |
| 5,593,388 | 1/1997 | Phillips | 604/131 |
| 5,593,390 | 1/1997 | Castellano et al. | 604/207 |
| 5,599,314 | 2/1997 | Neill | 604/207 |
| 5,688,251 | 11/1997 | Chanoch | 604/208 |

FOREIGN PATENT DOCUMENTS

| WO 092018179 | 10/1992 | WIPO | 604/187 |
|---|---|---|---|
| WO 093024160 | 10/1993 | WIPO | 604/208 |

*Primary Examiner*—Ronald Stright
*Assistant Examiner*—Jeremy Thissell
*Attorney, Agent, or Firm*—Alan W. Fiedler

[57] ABSTRACT

A medication delivery pen having a repeat-dose feature that is performed by using a pull-push operation. In particular, the medication delivery pen includes means for determining whether the medication delivery pen is armed and a variety of novel drive mechanisms. In addition, the medication delivery pen also includes a priming control mechanism that allows the user to easily prime medication delivery pen prior to arming the pen.

12 Claims, 13 Drawing Sheets

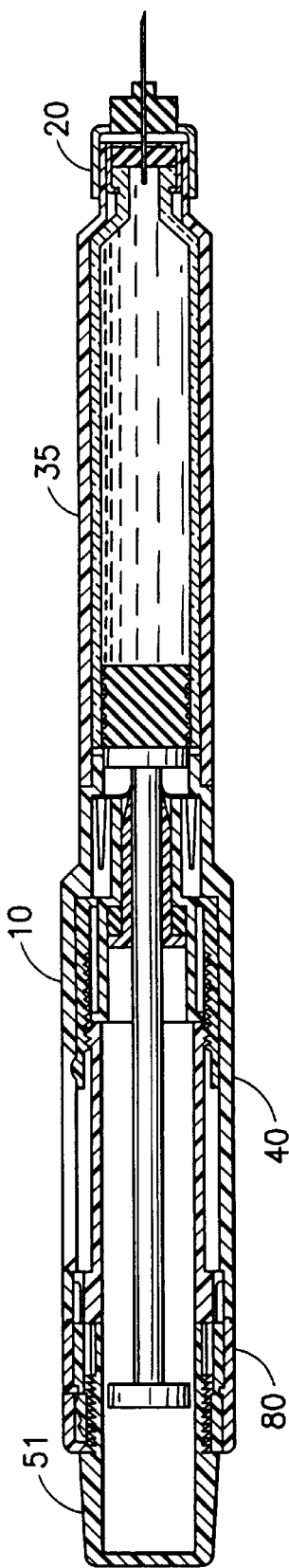
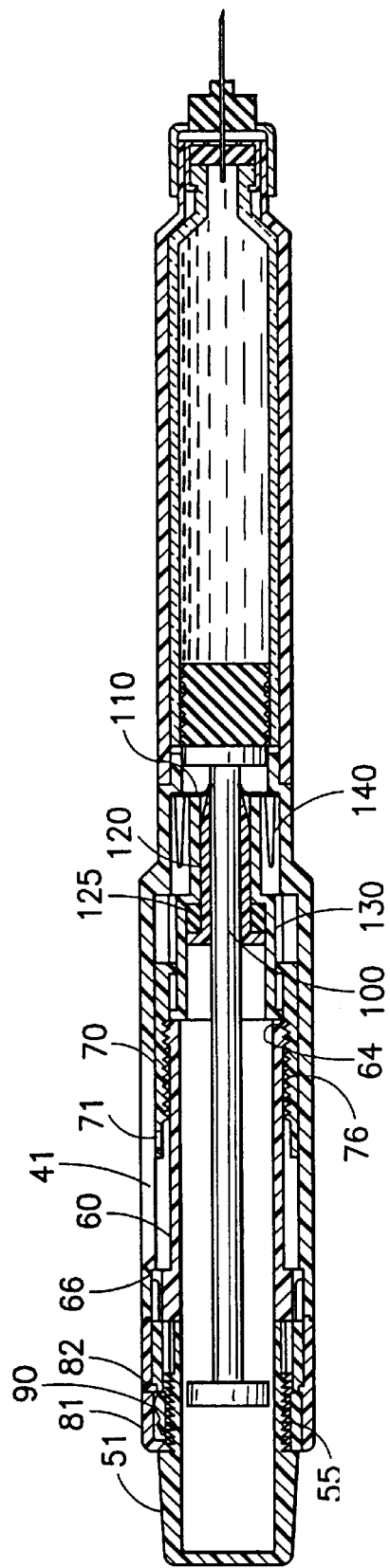
FIG.5
FIG.6

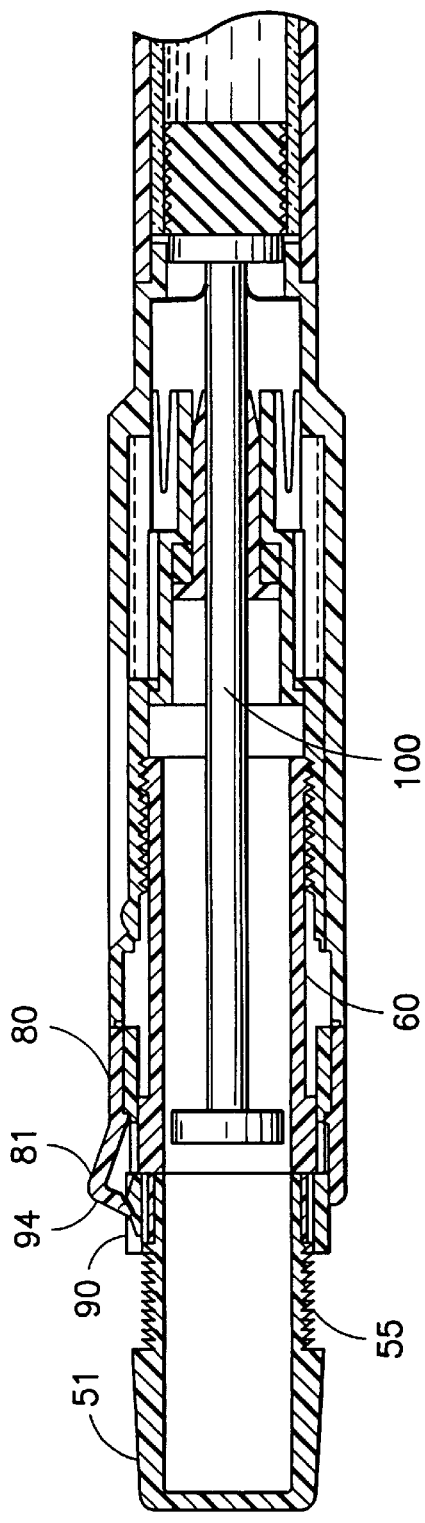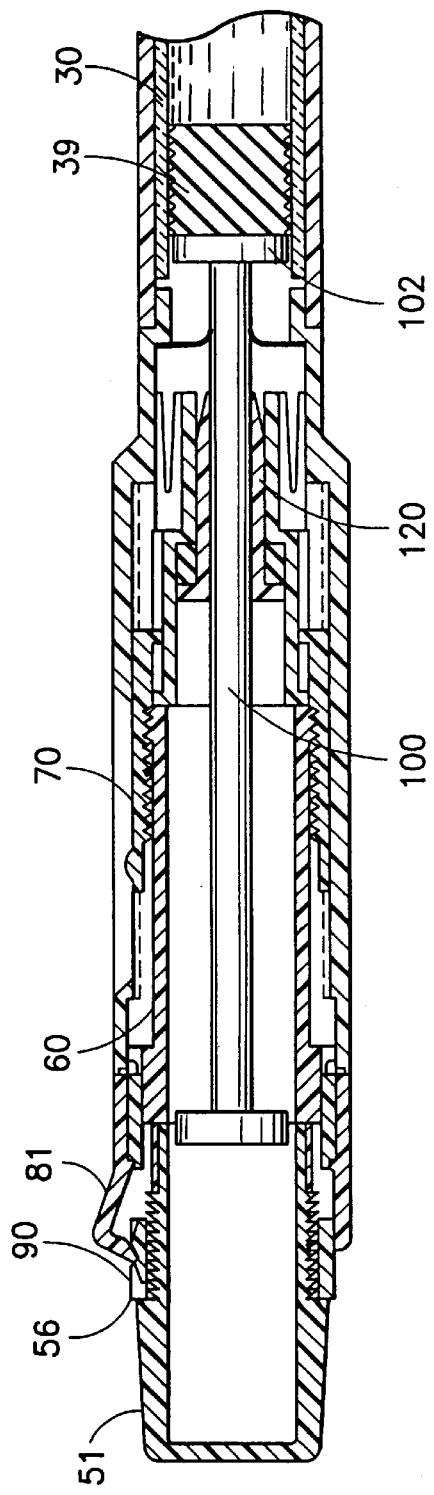

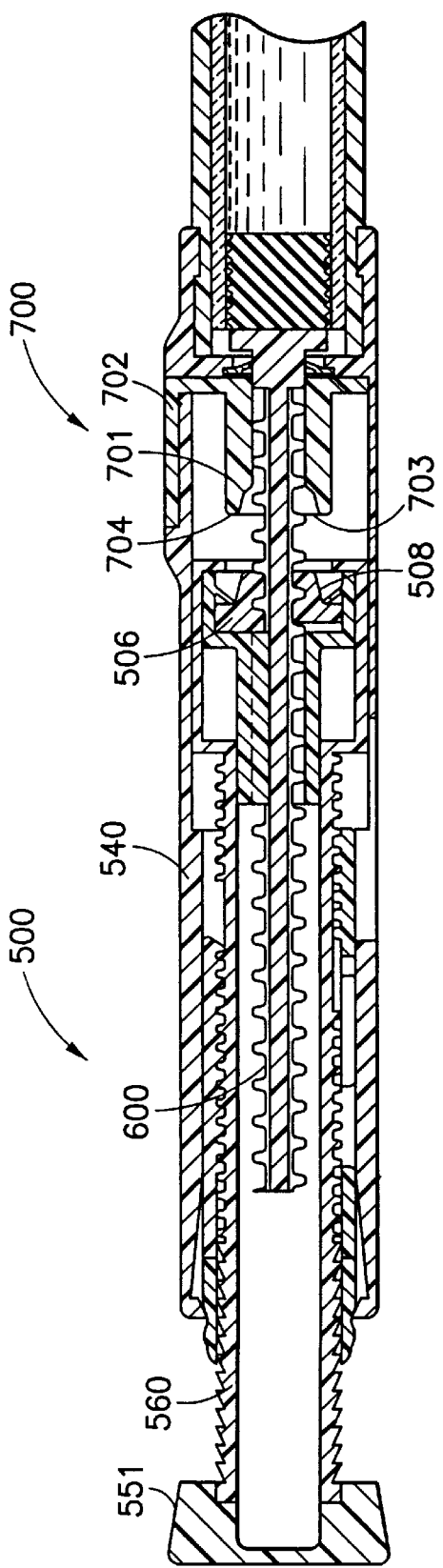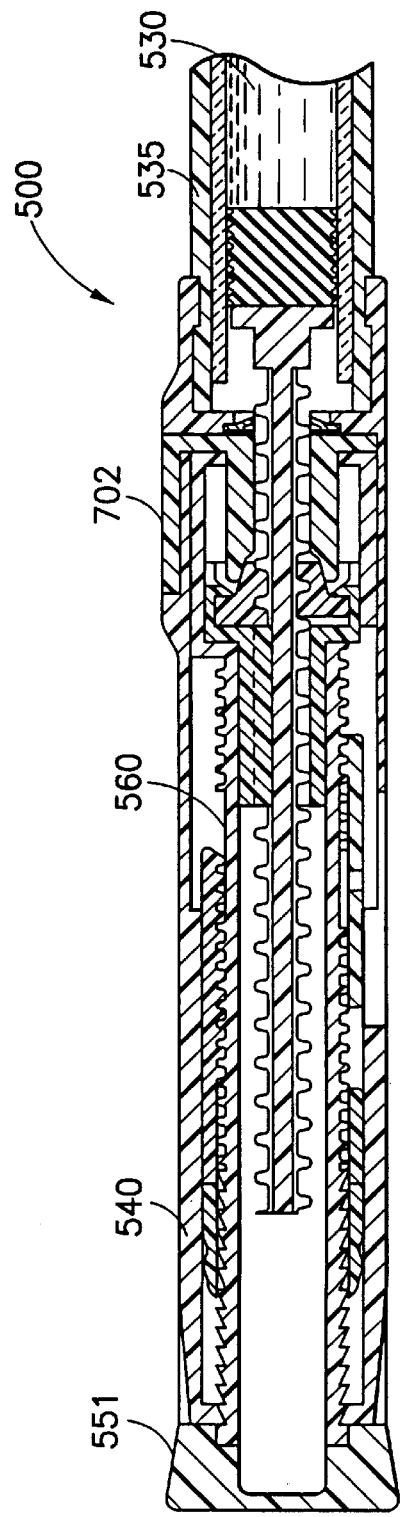
FIG. 17
FIG. 18

MEDICATION DELIVERY PEN HAVING A
PRIMING MECHANISM

BACKGROUND OF THE INVENTION

1. Field of the Invention

The present invention relates to a medication delivery having a priming control mechanism.

2. Description of Related Art

Hypodermic syringes are used to deliver selected doses of medication to patients. The prior art hypodermic syringe includes a syringe barrel having opposed proximal and distal ends. A cylindrical chamber wall extends between the ends and defines a fluid receiving chamber. The proximal end of the prior art syringe barrel is substantially open and receives a plunger in sliding fluid tight engagement. The distal end of the prior art syringe barrel includes a passage communicating with the chamber. A needle cannula may be mounted to the distal end of the prior art syringe barrel, such that the lumen of the needle cannula communicates with the passage and the chamber of the syringe barrel. Movement of the plunger in a proximal direction draws fluid through the lumen of the needle cannula and into the chamber. Movement of the plunger in a proximal-to-distal direction urges fluid from the chamber and through the lumen of the needle cannula.

Medication to be injected with the prior art hypodermic syringe often is stored in a vial having a pierceable elastomeric seal. Medication in the prior art vial is accessed by piercing the elastomeric seal with the needle cannula. A selected dose of the medication may be drawn into the chamber of the syringe barrel by moving the plunger a selected distance in a proximal direction. The needle cannula may be withdrawn from the vial, and the medication may be injected into a patient by moving the plunger in a distal direction.

Some medication, such as insulin is self-administered. The typical diabetes patient will require injections of insulin several times during the course of the day. The required dose of insulin will vary from patient to patient, and for each patient may vary during the course of the day and from day to day. Each diabetes patient will establish a regimen that is appropriate for his or her own medical condition and for his or her lifestyle. The regimen typically includes some combination of a slow or medium acting insulin and a faster acting insulin. Each of these regimens may require the diabetes patient to periodically self-administer insulin in public locations, such as places of employment or restaurants. The required manipulation of the standard prior art hypodermic syringe and vial can be inconvenient and embarrassing in these public environments.

Medication delivery pens have been developed to facilitate the self-administration of medication. One prior art medication delivery pen includes a vial holder into which a vial of insulin or other medication may be received. The vial holder is an elongate generally tubular structure with proximal and distal ends. The distal end of the prior art vial holder includes mounting means for engaging a double-ended needle cannula. The proximal end also includes mounting means for engaging a driver and dose setting apparatus as explained further below. A disposable vial for use with the prior art vial holder includes a distal end having a pierceable elastomeric seal that can be pierced by one end of a double-ended needle cannula. The proximal end of this prior art vial includes a plunger slidably disposed in fluid tight engagement with the cylindrical wall of the vial. This prior art medication delivery pen is used by inserting the vial of medication into the vial holder. A prior art pen body then is connected to the proximal end of the vial holder. The pen body includes a dose setting apparatus for designating a dose of medication to be delivered by the pen and a driving apparatus for urging the plunger of the vial distally for a distance corresponding to the selected dose.

The user of the pen mounts a prior art double-ended needle cannula to the distal end of the vial holder such that the proximal point of the needle cannula pierces the elastomeric seal on the vial. The patient then selects a dose and operates the pen to urge the plunger distally to deliver the selected dose. The dose selecting apparatus returns to zero upon injection of the selected dose with this prior art medication delivery pen. The patient then removes and discards the needle cannula, and keeps the prior art medication delivery pen in a convenient location for the next required medication administration. The medication in the vial will become exhausted after several such administrations of medication. The patient then separates the vial holder from the pen body. The empty vial may then be removed and discarded. A new vial can be inserted into the vial holder, and the vial holder and pen body can be reassembled and used as explained above.

The above described reusable medication delivery pen is effective and much more convenient for self-administration of medication than the hypodermic syringes that use separate medication vials. However, the above described medication delivery pen requires a user to continually set or reset the desired dose before each injection. As a result, users with impaired vision and fine motor skills have found it difficult to readily set the dose on such pens especially when using a medication delivery pen having a wide range of dosage settings available. Since it is particularly common among patients with diabetes to have complications of the disease causing impaired vision and fine motor skills even more of a need has been found to address this problem. Hence, it is necessary to provide a medication delivery pen having a simple mechanism for setting the desired dose and, more preferably, a dose delivery mechanism having a repeat-dose capability.

SUMMARY OF THE INVENTION

The present invention relates to a medication delivery pen that addresses the above-identified problem.

The medication delivery pen includes a pen-needle assembly, a vial retainer including a vial containing a medication to be delivered, and a housing. The housing includes a dose control mechanism for editing a desired dose to be delivered from the medication delivery pen, a drive mechanism for dispensing the desired dose from the medication delivery pen when the medication delivery pen is in an armed condition, and means for armed drive mechanism using a push-pull operation. In addition, the medication delivery pen also includes means for indicating whether the drive mechanism is in the armed position.

Another advantage of the medication delivery pen according to the present invention is that it includes a priming control mechanism that allows the user to easily prime the medication delivery pen prior to arming the pen.

These and other aspects, features and advantages of the present invention will become apparent from the following detailed description taken in conjunction with the accompanying drawings.

BRIEF DESCRIPTION OF THE DRAWINGS

FIG. 5 is a cross-sectional view of the medication delivery pen shown in FIG. 1 in a ready for use condition.

FIG. 6 is a cross-sectional view of the medication delivery pen shown in FIG. 1 in a dialing condition.

FIG. 7 is a cross-sectional view of the medication delivery pen shown in FIG. 1 in an armed position.

FIG. 8 is a cross-sectional view of the medication delivery pen shown in FIG. 1 in a dispensing position.

FIG. 17 is a cross-sectional view of the medication delivery pen shown in FIG. 15 in an armed condition.

FIG. 18 is a cross-sectional view of the medication delivery pen shown in FIG. 15 in an end of travel or dispensed condition.

DETAILED DESCRIPTION OF THE INVENTION

Figure 1:
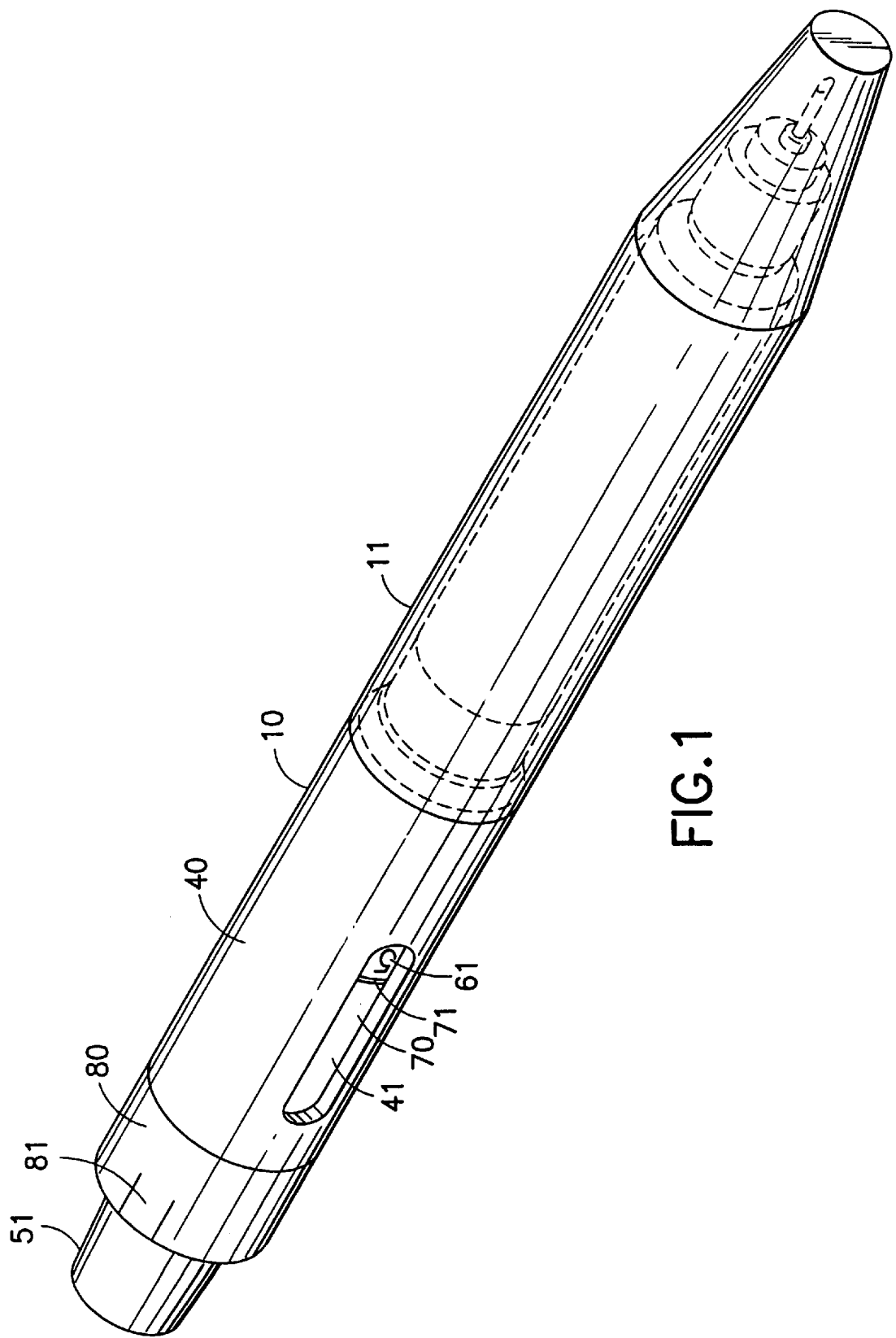
FIG. 1 is a perspective view of a repeat-dose medication delivery pen according to the present invention.

A repeat-dose medication delivery pen 10 according to the present invention is shown in FIG. 1. Medication delivery pen 10 includes a cap 11 removeably attached to a housing 40 having a dose knob 51 axially and rotatably mounted thereon. As shown in FIG. 1, housing 40 includes a longitudinally extending viewing port 41 through which an outer surface of dose window 70 is shown together with a viewing hole 71 extending through dose window 70. Through viewing hole 71 and viewing port 41 one of a plurality of dosage numerals 61 printed on a dose barrel 60, discussed below, is visible to a user. Either viewing port 41 or viewing hole 70 may incorporate a magnifying lens to enlarge dosage numeral 61 to increase readability of these numerals. In addition, FIG. 1 shows means for indicating whether medication delivery pen 10 is armed and ready for medication dispensing as well as indicating when medication has been properly dispensed as represented by a dosing pawl 81 that extends radially from an outer surface of pawl housing 80.

Figure 2:
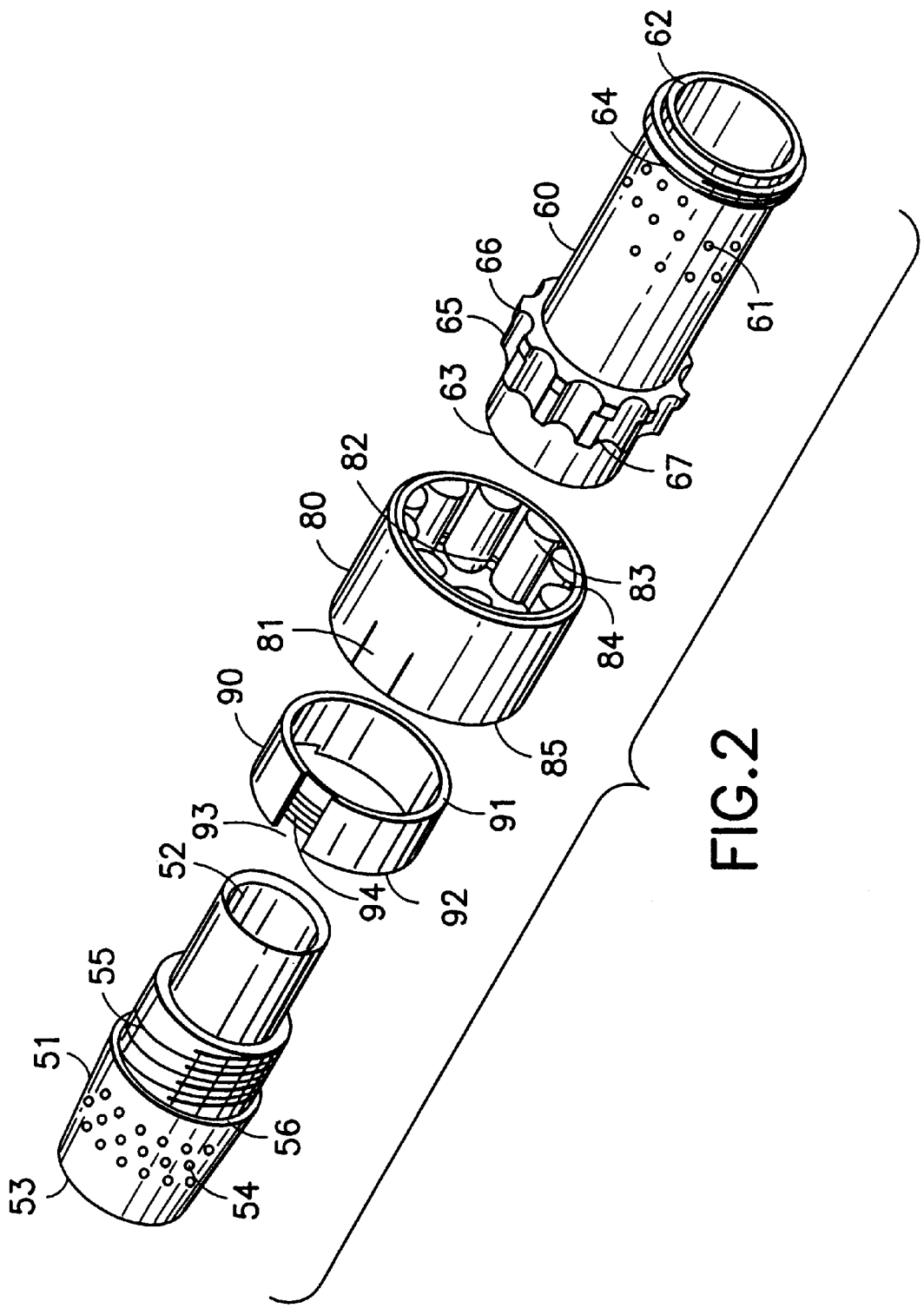
FIGS. 2–4 are exploded perspective views of the medication delivery pen shown in FIG. 1.
Figure 3:
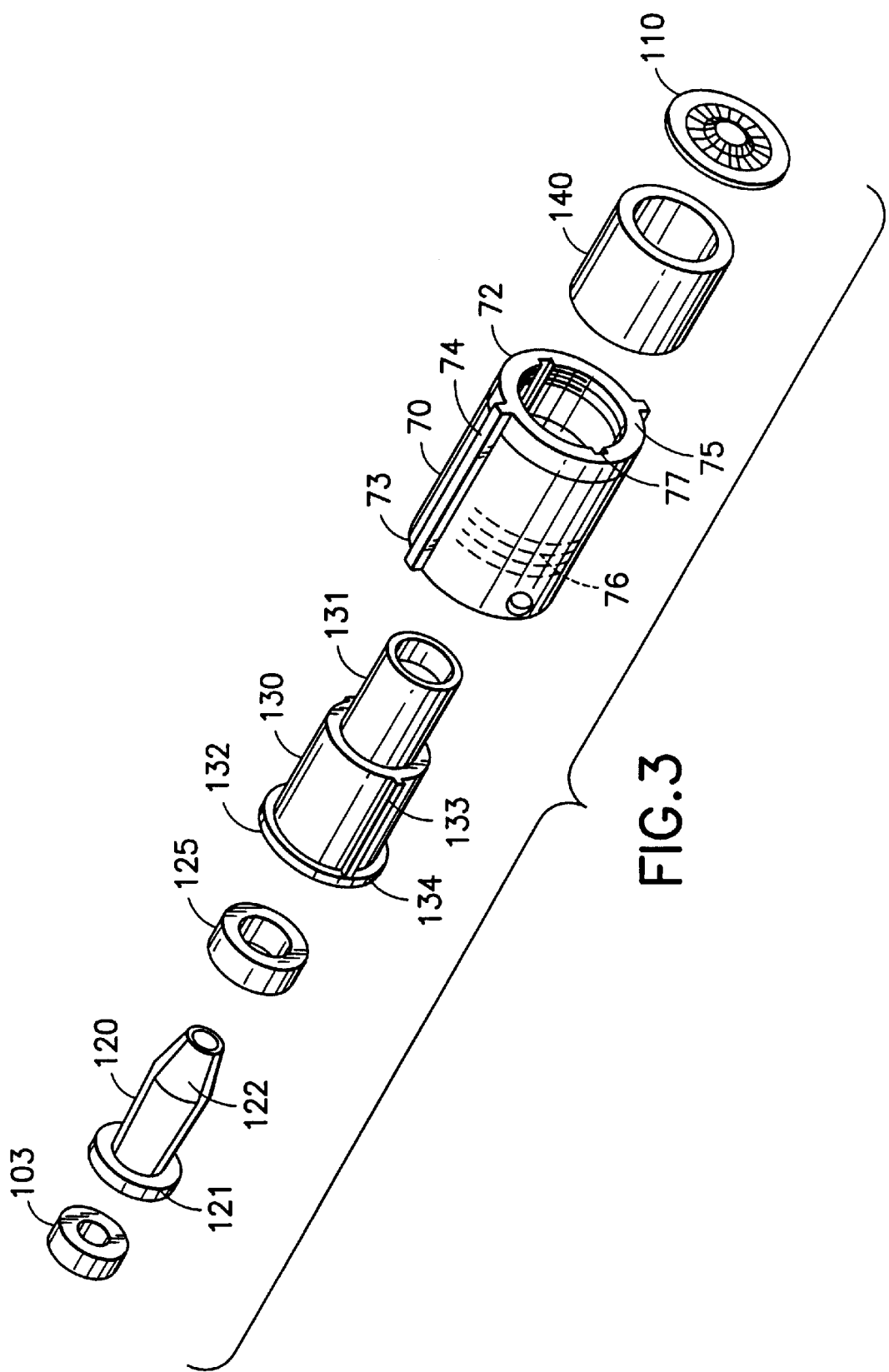
Figure 4:
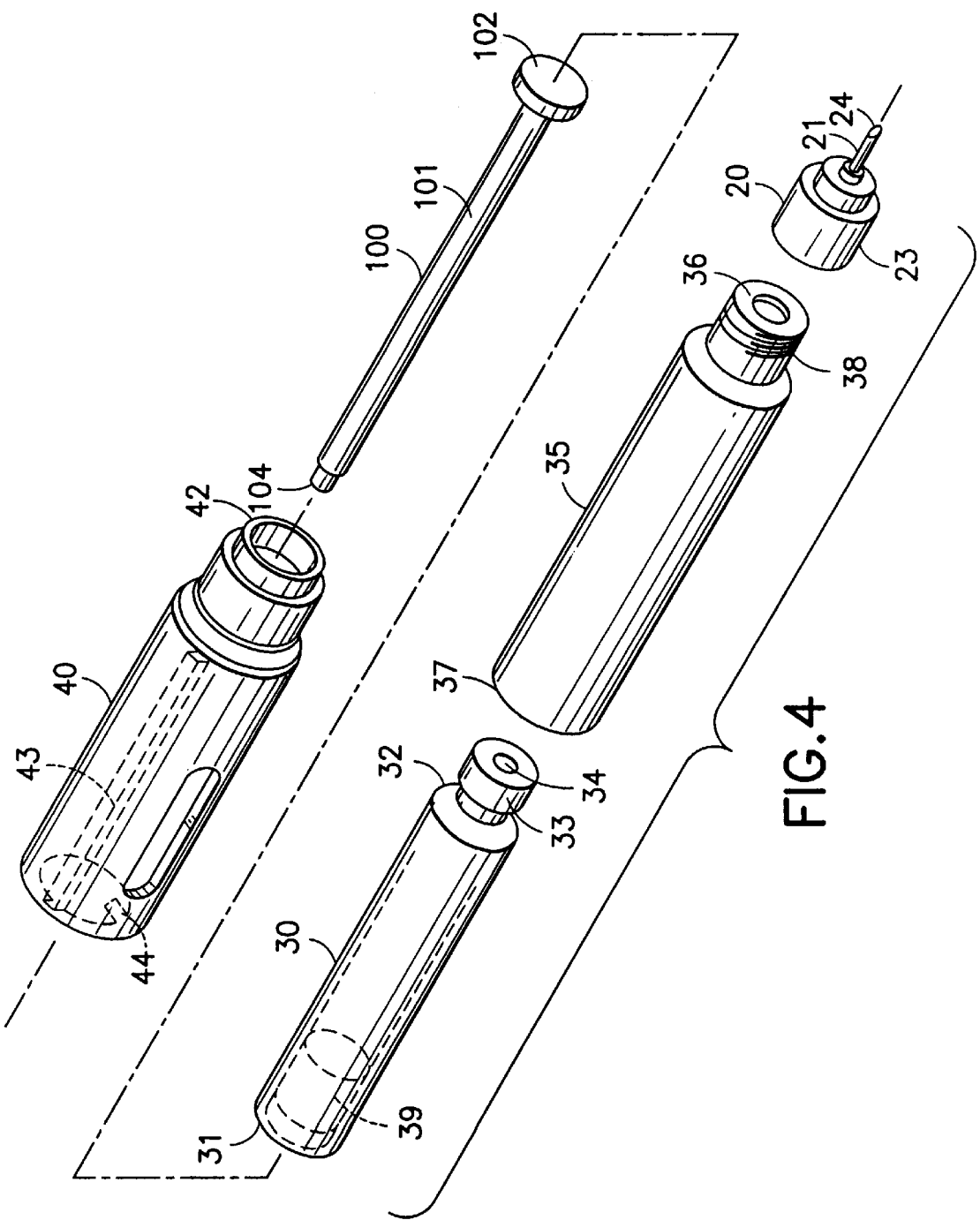

FIGS. 2–4 show an exploded perspective view of medication delivery pen 10 and, more particularly, FIG. 4 shows a pen-needle assembly 20 that is releasably engaged to a distal end 36 of a vial retainer 35. Pen-needle assembly 20 includes a double-ended needle cannula 21 having a distal point 24 and a proximal point (not shown). Double-ended needle cannula 21 is mounted in a hub 23 including means for attaching hub 23 to distal end 36 of vial retainer 35. Vial retainer 35 includes distal end 36 and proximal end 37 with a set of threads 38 surrounding distal end 36 that are used to engage with similar threads (not shown) in hub 23 of pen-needle assembly 20.

Proximal end 37 of vial retainer 35 includes an opening that receives a vial 30 when medication delivery pen 10 is assembled. Vial 30 includes a proximal end 31 and a distal end 32 having a vial cap 33 that securely holds a vial septum 34 on distal end 32. Vial 30 also includes a vial piston 39 therein to form a sterile sliding seal within vial 30 to hold medication therein. When pen-needle assembly 20 is mounted on vial retainer 35, the proximal point of needle cannula 21 pierces vial septum 34 to provide a fluid flow path from the interior of vial 30 through cannula 21 during a dispensing operation.

FIGS. 2–4 also show medication delivery pen 10 and, more particularly, the drive mechanism, dosing control mechanism and means for indicating whether medication delivery pen 10 is armed. The drive mechanism is comprised of a plunger 100 having a shaft 101 extending from a proximal plunger face 102 to a proximal end 104 that receives a plunger stop 103 when the drive mechanism is fully assembled. Plunger 100 extends from a distal end 42 of housing 40 and has mounted thereon a star washer 110, a collet-housing interface 140 that slideably mounts on a distal end 131 of a collet-housing 130 that receives in its proximal end 132 a collet spring 125 and a collet 120. Collet 120 includes a distal flange 121 and a plurality of fingers 122 extending in a proximal direction and dimensioned to receive collet spring 125 thereon. Collet spring 125 and fingers 122 are received in proximal end 132 of collet housing 130 as collet 120 is slideably mounted on plunger shaft 101 during assembly period. Collet housing 130 also includes a collet housing flange 134 at proximal end 132 and a pair of collet housing keys 133 extending from its outer surface.

FIGS. 2–4 also show the dosing control mechanism that is comprised of a dose knob 51, a dose barrel 60 and a dose window 70. Dose window 70 includes an open distal end 72 and an open proximal end 73 with an anti-rotation key 74 extending radially from the outside surface of dose window 70. A dose window flange 75 extends into dose window 70 near open distal end 72 and a set of threads 76 are on the inner diameter of dose window 70 near open proximal end 73. Dose window flange 75 includes a pair of dose window keyways 77 that receive collet housing keys 133 on the outside of collet housing 130 when collet housing 130 is inserted into dose window 70.

Keyway 77 and keys 133 work together to prevent collet housing 130 from rotating with respect to dose window 70. Dose window 70 also includes a pair of anti-rotation keys 74 that are received in a pair of keyways 43 within housing 40 to prevent dose window 70 and collet housing 130 from rotating with respect to housing 40. Of course, collet housing 130 can move axially with respect to dose window 70 and both of these components can move axially with respect to housing 40.

Dose barrel 60 includes an open distal end 62 and an open proximal end 63, with a set of external threads 64 near open distal end 62 that engage with thread 76 within dose window 70. Threads 64 and 76 are used to establish the dose being set by the dosing control mechanism in medication delivery pen 10. Dose barrel 60 includes a plurality of dose barrel keys 65 extending from an outer surface that includes a plurality of shoulders 67 that are used to push a sliding sleeve 90, discussed below, and travel stops 66 that interacts with a rear stop 82, discussed below, when medication delivery pen 10 is armed and ready for dispensing.

Dose knob 51 includes an open distal end 52 and a closed proximal end 53 having an outside surface that is textured 54 or includes an indentation to provide easy operator manipulation of dose knob 51 during dose setting and arming of the medication delivery pen 10. Dose knob 51 also includes a plurality of dosing ratchets 55 circumferential to dose knob 51 and adjacent to an edge 56 extending from the outer surface of dose knob 51. Distal end 52 of dose knob 51 is received within open proximal end 63 of dose barrel 60 and permanently mounted therein.

In addition, the dosing control mechanism is received within housing 40 such that a clicker 44 extending radially inward from an inner surface of housing 40 is aligned with and over key 65 on the exterior surface of dose barrel 60 to provide audible and/or tactile feedback during dose increment settings.

When dose knob 51 is mounted within dose barrel 60 it receives sliding sleeve 90 and a pawl housing 80 thereon that provides means for indicating whether or not the medication delivery pen 10 is armed. Pawl housing 80 includes an open distal end 84 and an open proximal end 85 having rear stop 82 near proximal end 85 and a plurality of keyways 83 formed around the inner circumference of pawl housing 80. Keyways 83 are shaped to receive key 65 on dose barrel 60 when medication delivery pen 10 is armed to prevent modification of the set dose when the medication delivery pen 10 is armed. Pawl housing 80 also includes a plurality of dosing pawls 81 that extend in the proximal direction and moves radially from the surface of pawl housing 80 when medication delivery pen 10 is armed. Sliding sleeve 90 includes a distal face 91 and a proximal face 92 with a plurality of grooves 93 extending therebetween on the outer surface of sliding sleeve 90. Each groove 93 includes a detent 94 that receives a respective dosing pawl 81 when medication delivery pen 10 is armed, thereby providing means for indicating the armed condition and that medication delivery pen 10 is ready for dispensing.

FIGS. 5–9 show a variety of conditions through which medication delivery pen 10 moves during dose setting, arming and dispensing. FIG. 5 shows medication delivery pen 10 in a ready for use condition from which it is then moved during a dialing condition shown in FIG. 6. During dialing, dose knob 51 is rotated to set the desired dose of medication to be delivered by medication delivery pen 10. This rotation produces a linear movement of dose window 70 relative to dose barrel 60 on which the plurality of dosage numerals are printed or inscribed. Movement of dose window 70 in the proximal direction changes the dose amount displayed through a rotational movement. This is achieved by thread 76 within dose window 70 interfacing with thread 64 on the exterior of dose barrel 60 and dose window 70 being keyed by key 74 and keyway 43 to housing 40. Therefore, when dose knob 51 is rotated relative to housing 40, dose window 70 is constrained from rotation and moves only in the proximal or distal direction.

When the desired dose increment is displayed through viewing hole 71 and viewing port 41, dose knob 51 and dose barrel 60 are then moved proximally, which also moves dose window 70, collet 120, collet spring 125, collet housing 130, and collet-housing interface 140 proximally. The amount of proximal movement is established by the linear axially distance between travel stop 66 on dose barrel 60 and rear stop 82 within pawl housing 80. Of course, rear stop 82 could be replaced with any stop on pawl housing 80 or another component that does not move relative to pawl housing 80 during normal operation. The amount of proximal motion of collet 120 is proportional to the desired dose being set by rotation of dose knob 51 and dose barrel 60. During proximal movement of dose knob 51, dose barrel 60, dose window 70 and collet 120, plunger 100 is prevented from moving proximally by starwasher 110. During proximal and distal motion of dose knob 51, dose barrel 60 and dose window 70, the position of dose window 70 relative to dose barrel 60 is maintained such that the dosage numeral visible through viewing hole 71 and viewing port 41 is unchanged and is continually visible to the user.

To ensure proper and complete axial motion during arming of medication delivery pen 10 by the dosing control mechanism including dose knob 51, dose barrel 60 and dose window 70, dosing ratchets 55 on dose knob 51 and dosing pawl 81 on pawl housing 80 are used. Dosing ratchet 55 interfaces with dosing pawls 81 so as to prevent distal motion of the drive mechanism including plunger 100 until medication delivery pen 10 has been fully armed. Dosing ratchet 55 on dose knob 51 moves within sliding sleeve, collar or ring 90 until sliding sleeve 90 encounters shoulder 67 on dose barrel 60. Shoulder 67 then causes sliding sleeve 90 to move in a proximal direction, away from pawl housing 80. Sliding sleeve 90 and the dosing control mechanism then move together in a proximal direction as the dosing control mechanism nears the end of its proximal travel.

Sliding sleeve 90 includes a plurality of grooves including detent 94 that moves dosing pawls 81 radially away from dose barrel 60, dose knob 51 and pawl housing 80, and that engage dosing pawls 81 to finally allow the drive mechanism including plunger 100 to move in the distal direction. Motion of sliding sleeve 90 and engagement of dosing pawls 81 into detent 94 also provides an indication to the user that the dosing control mechanism has been properly and fully placed in the armed position for proper dose delivery. Sliding sleeve 90 is preferably of a color that improves the level of visual indication, e.g., green. In addition, engagement of dosing pawls 81 and detents 94 provides an audible and/or tactile feedback to provide additional indication to the user that the medication delivery pen 10 is fully armed. FIG. 7 shows medication delivery pen 10 in this fully armed condition.

After medication delivery pen 10 has been fully armed, dose knob 51 is pushed in the distal direction, which causes distal motion of dose barrel 60, dose window 70, collet 120 and plunger 100 such that plunger face 102 displaces vial piston 39 within vial 30 to deliver the desired dose of medication through double-ended cannula 21. This dispensing condition of medication delivery pen 10 is shown in FIG. 8. Upon distal motion of the dosing control mechanism, dose knob edge 56 pushes sliding sleeve 90 back into its original position when dosing control mechanism 50 is at the end of travel or dispensed condition shown in FIG. 9. This distal motion of sliding sleeve 90, disengages dosing pawls 81 from detent 94 on sliding sleeve 90 with audible and/or tactile indication that provides additional feedback to the user that the full intended dose has been delivered. In addition, disappearance of sliding sleeve 90 within pawl housing 80 provides visual feedback to the user that the full dose has been delivered.

Figure 9:
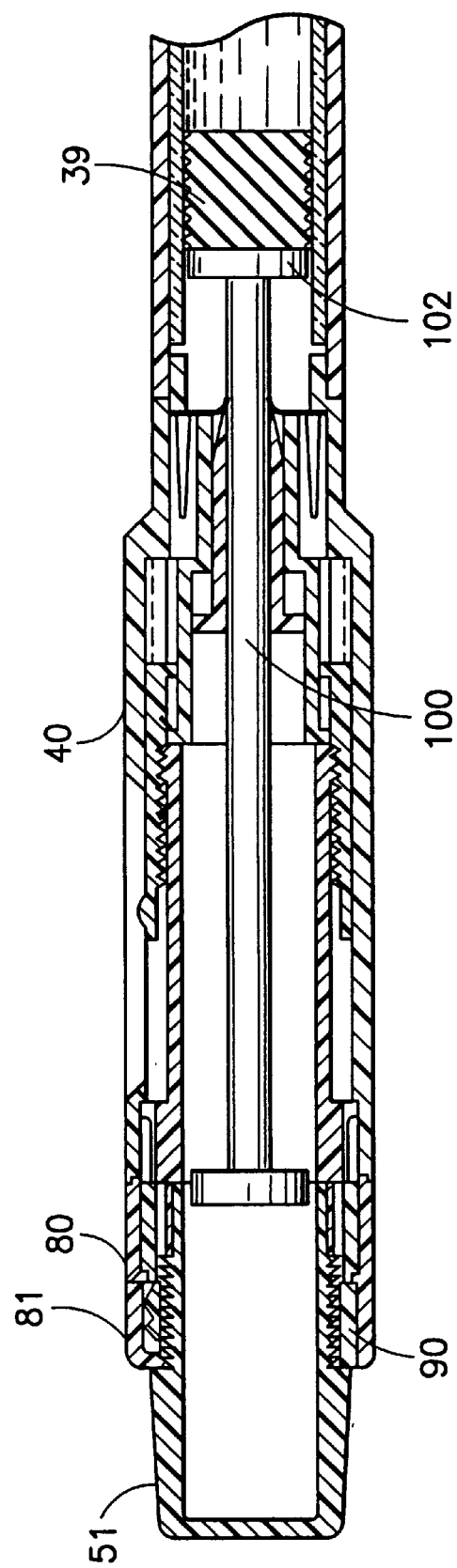
FIG. 9 is a cross-sectional view of the medication delivery pen shown in FIG. 1 in an end of travel or dispensed condition.

To prevent rotation during distal and proximal movement of dose barrel 60, as discussed above, keys 65 on dose barrel 60 and keyways 83 within pawl housing 80 prevent rotation of the dosing control mechanism unless dose knob 51 is in the end of travel or dispensed condition shown in FIG. 9.

To deliver another dose of the same amount, no rotation of the dosing control mechanism is required, since the relationship and distance between flange 132 of collet housing 130 and dose window flange 75 on dose window 70 has been previously established.

Figure 10:
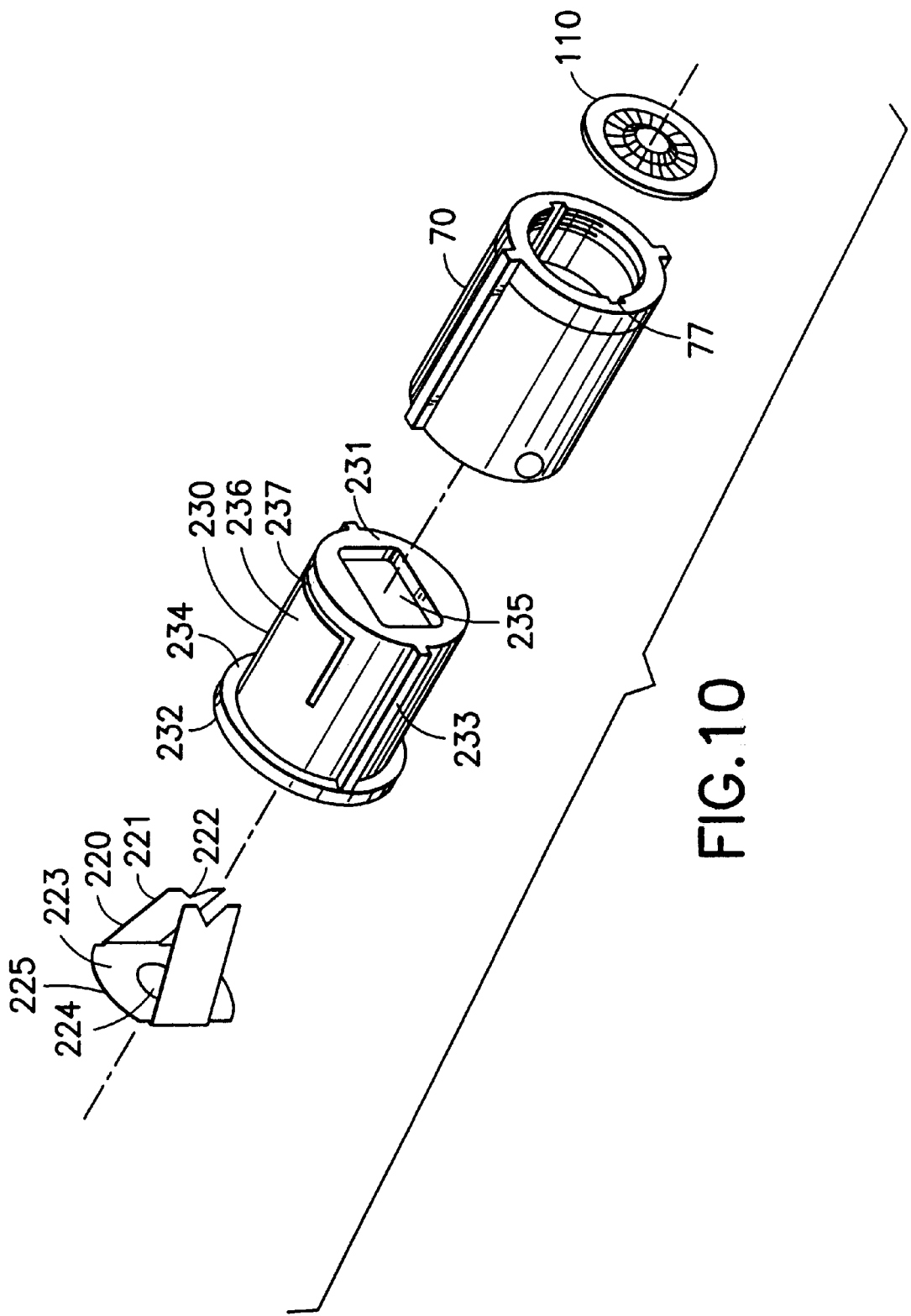
FIG. 10 is an exploded perspective view of an alternative repeat-dose medication delivery pen according to the present invention having a spring clip in place of the collet assembly shown in FIG. 3.

FIG. 10 is an exploded perspective view of an alternative repeat-dose medication delivery pen according to the present invention having a spring clip 220 in place of the collet assembly as shown in FIG. 3. FIG. 10 shows dose window 70 and star washer 110 that are substantially the same as those used in the earlier embodiment and shows spring clip 220 having a pair of spring clip fingers 221 extending in the distal direction and radial inward to a gripping feature 222 on each spring clip finger 221. A spring clip flange 223 is attached to proximal end of each spring clip finger 221 and includes a through hole for receiving plunger shaft 101 of plunger 100. FIG. 10 also shows a spring clip housing 230 having a housing flange 234 at its proximal end 232 and an opening 235 through its distal end 231. Spring clip housing 230 also includes a pair of tabs 236 having a distal notch 237 for receiving each edge 225 on flange 223 of spring clip 220. In addition, spring clip housing 230 includes a pair of spring clip housing keys 233 extending from the outer surface of spring clip housing 230 for engaging keyways 77 within dose window 70.

Spring clip 220 and spring clip housing 230 provides the same features that the collet assembly in the earlier embodiment provides by using a pair of spring clip fingers 221 to grab plunger shaft 101 and move plunger 100 in a distal direction, such that plunger face 102 displaces vial piston 39 with vial 30 to deliver the desired dose of medication through double-ended cannula 21.

Figure 11:
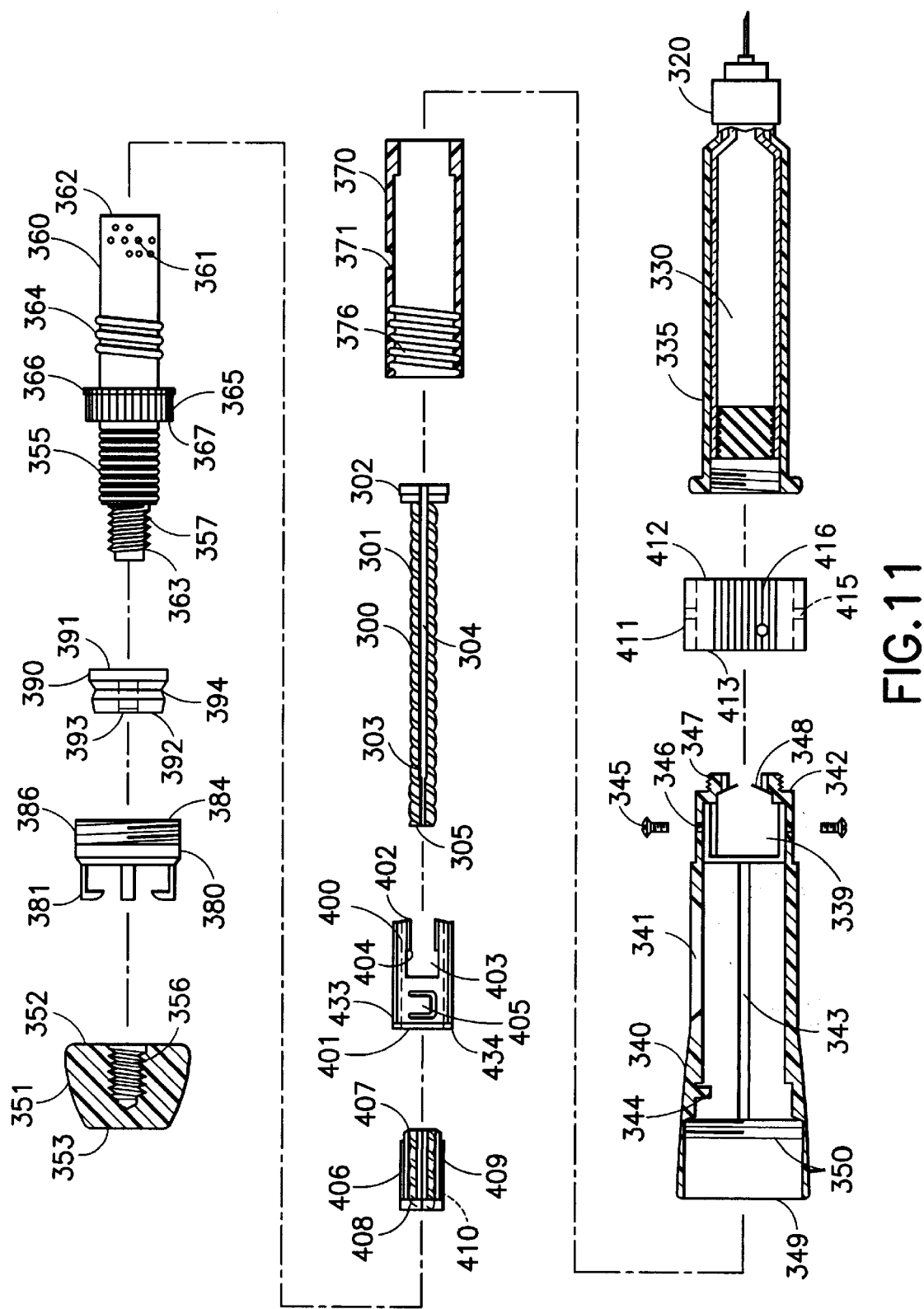
FIG. 11 is an exploded cross-sectional view of another embodiment of a repeat-dose medication delivery pen according to the present invention.

FIG. 11 is an exploded cross-sectional view of another embodiment of a repeat-dose medication delivery pen according to the present invention. As shown in FIG. 11 the medication delivery pen includes a pen-needle assembly 320, a vial 330, and a vial retainer 335. Vial retainer 335 is attached to a set of threads 347 at a distal end 342 of a housing 340, which includes a longitudinally extending viewing port 341 through which an outer surface of a dose window 370 is substantially the same as dose window 70 in the earlier embodiment as seen by the user. Dose window 370 includes a viewing hole 371 through which a plurality of dosage numerals 361 on a dose barrel 360 are visible to the user. As in the earlier embodiment, FIG. 11 shows means for indicating the medication delivery pen is armed and ready for medication dispensing as well as indicating when medication has been properly dispensed, but uses a pawl assembly 380 having a plurality of dosing pawls 381 that extend radially from an outer surface of pawl assembly 380.

Figure 14:
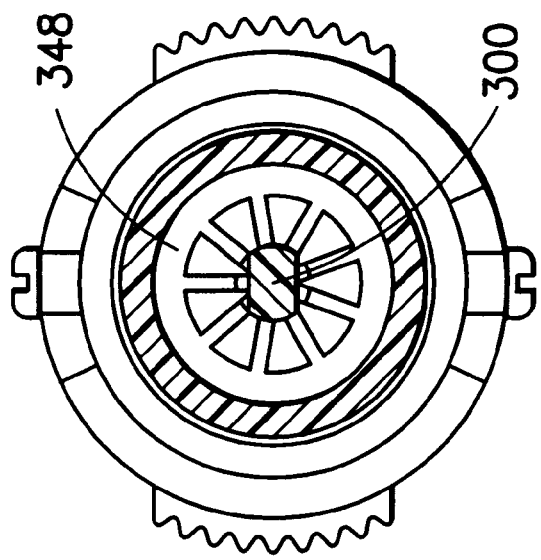
FIG. 14 is another cross-sectional view of the medication delivery pen shown in FIG. 12, at lines 14—14.

Housing 340 also includes a clicker 344 that engages a plurality of dose barrel keys on a dose barrel 360 to provide audible and/or tactile feedback during dose increment settings, as described in the earlier embodiment. Housing 340 also includes near its distal end 342 a star washer 348, also shown in FIG. 14, that performs substantially the same function as star washer 48 in the earlier embodiment. A set of threads 350 are located near a proximal end 349 of housing 340 that engage with a set of threads 383 on a distal end 384 of pawl assembly 380. Of course, this means of attaching pawl assembly 380 to housing 340 is merely exemplary and other means of attaching could be used and still followed in the scope of the present invention.

Figure 12:
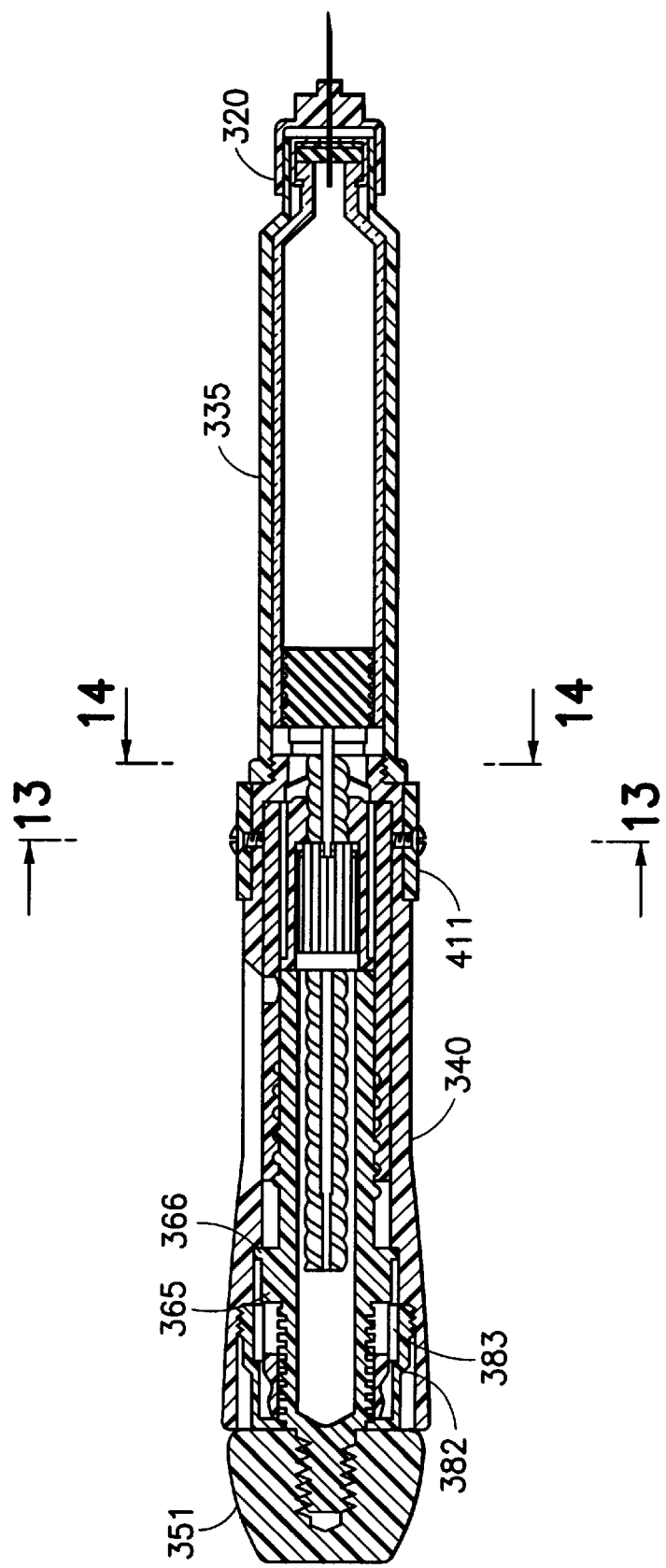
FIG. 12 is a cross-sectional view of the medication delivery pen shown in FIG. 11 fully assembled.

FIG. 11 also shows a dose barrel 360 having a distal end 362 and a proximal end 363 with dosage numerals 361 on its outside surface near distal end 362 and a set of dosage threads 364 that mate with a set of dosage threads 376 within dose window 370 to perform as described in the earlier embodiment. In contrast to the earlier embodiment, dose barrel 360 includes a dosing ratchet 355 and a set of dose knob attachments for threads 357 located near proximal end 363, whereby a dose knob 351 having a set of internal threads 356 is attached to dose barrel 360. Dose knob 351 also includes a distal surface 352 and a proximal end 353. Dose barrel 360 also includes a plurality of dose barrel keys 365 extending from its outer surface that includes a plurality of shoulder 367 that are used to push a sliding collar 390, discussed below, and a travel stop 366 interacts with a rear stop 382, shown in FIG. 12, when the medication delivery pen is armed and ready for dispensing.

When dose knob 351 is threadably attached to dose barrel 360, dose barrel 360 receives sliding collar 390 and pawl assembly 380 thereon to provide means for indicating whether or not the medication delivery pen is armed. Pawl assembly 380 includes an open distal end 384 and a rear stop 382 therein and a plurality of keyways 383 formed around an inner circumference of pawl assembly 380. Keyways 383 are shaped to receive keys 365 on dose barrel 360 when medication delivery pen is armed to prevent modification of the set dose. Sliding collar 390 includes a distal face 391 and a proximal face 392 with a plurality of grooves 393 extending therebetween on the outer surface of sliding collar 390. In addition, sliding collar 390 includes a circumferencial detent 394 that receives dosing pawl 381 when the medication delivery pen is armed, thereby providing means for indicating the armed condition and that medication delivery pen is ready for dispensing.

The operation of pawl assembly 380, sliding collar 390, and dosing ratchet 355 is substantially similar to pawl housing 80, sliding sleeve 90, and dosing ratchet 55 on dose knob 51 in the earlier embodiment. An important difference between the earlier embodiment and the current embodiment is the use of a threaded plunger 300 having a threaded shaft 301 with a pair of longitudinal slots 304 extending from plunger face 302 to a rear slot edge 303 near a proximal end 305. Threaded plunger 300 meets with matching thread 410 within a ratchet nut 406 having a distal end 407 and a proximal end 408 with plurality of axial ratchets around the outside surface ratchet nut 406. Ratchet nut 406 is received within a proximal opening 401 of a ratchet housing 400 until it rests against an inner shoulder 404 within ratchet housing 400 near a distal end 402. Ratchet housing 400 also includes a pair of ratchet pawls 405 that interface with axial ratchet 409 on ratchet nut 406 to prevent ratchet nut 406 from rotating in one direction within ratchet nut housing 400. Ratchet nut housing 400 also includes a pair of openings 403 that provide access to axial ratchet 409 on ratchet nut 406.

Figure 13:
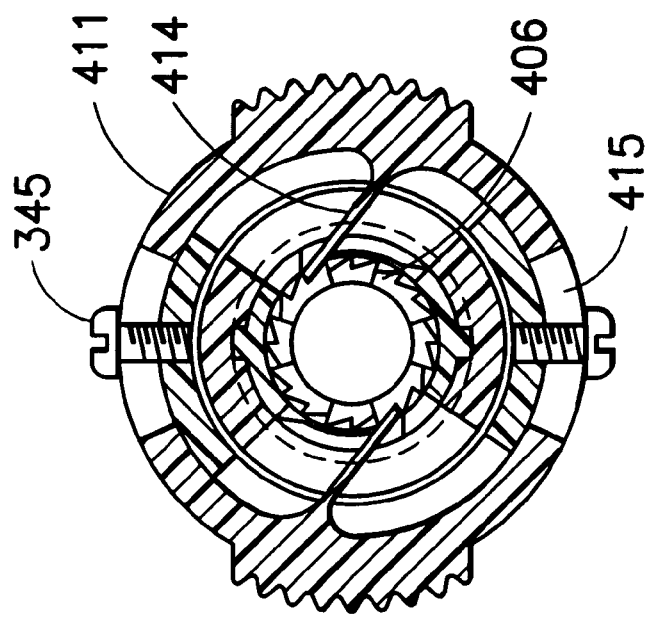
FIG. 13 is a cross-sectional view of the medication delivery pen shown in FIG. 12, at lines 13—13.

In addition, the alternative medication delivery pen includes a primary mechanism including a priming control sleeve 411 having an open distal end 412 and an open proximal end 413 with a set of gripping features 416 on its outer surface and a set of circumferencial slots that receive such screws 345 mounted and threaded in hole 346 near distal end 342 of housing 340. Circumferencial slots 415 are dimensioned to allow priming control sleeve 411 to rotate about housing 340. Priming control sleeve 411 also includes a plurality of priming pawls 414, shown in FIG. 13, extending therein that interact with ratchet 409 on ratchet nut 406 to rotate ratchet nut 409 and cause plunger 300 to move in the distal direction to prime the medication delivery pen. Priming pawls 414 extend through opening 339 near distal end 342 of housing 340 and through opening 403 in ratchet nut housing 400 to access ratchet 409 on ratchet nut 406. Of course, priming control sleeve 411 is merely exemplary and is not required to be a fully closed sleeve.

Figure 15:
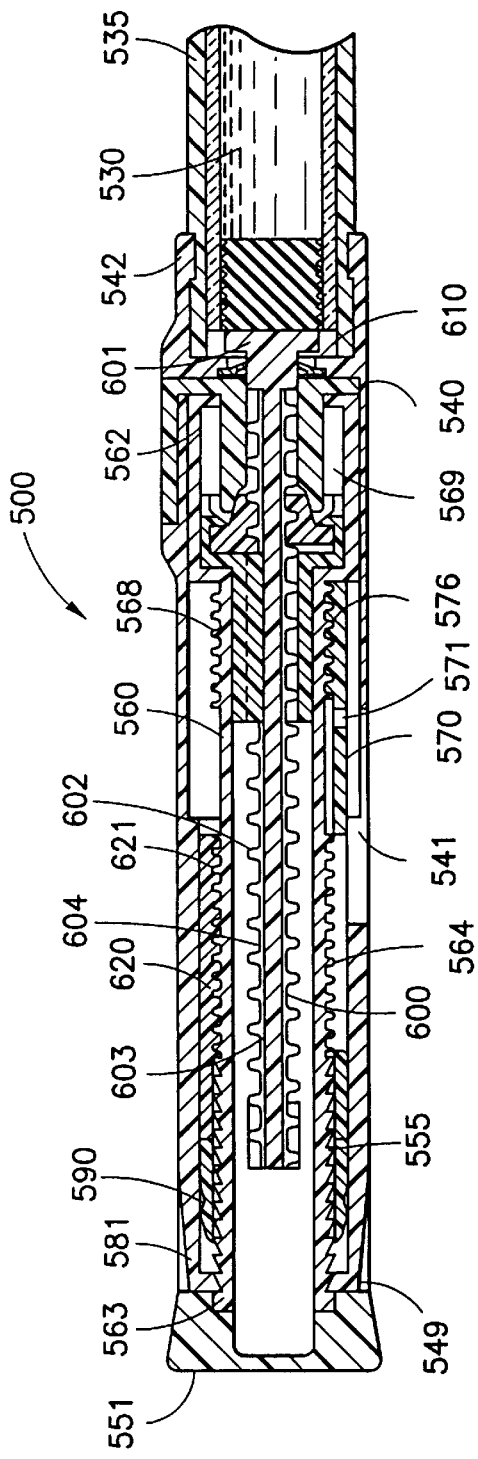
FIG. 15 is a cross-sectional view of yet another embodiment of a repeat-dose medication delivery pen according to the present invention in a ready for use condition.
Figure 16:
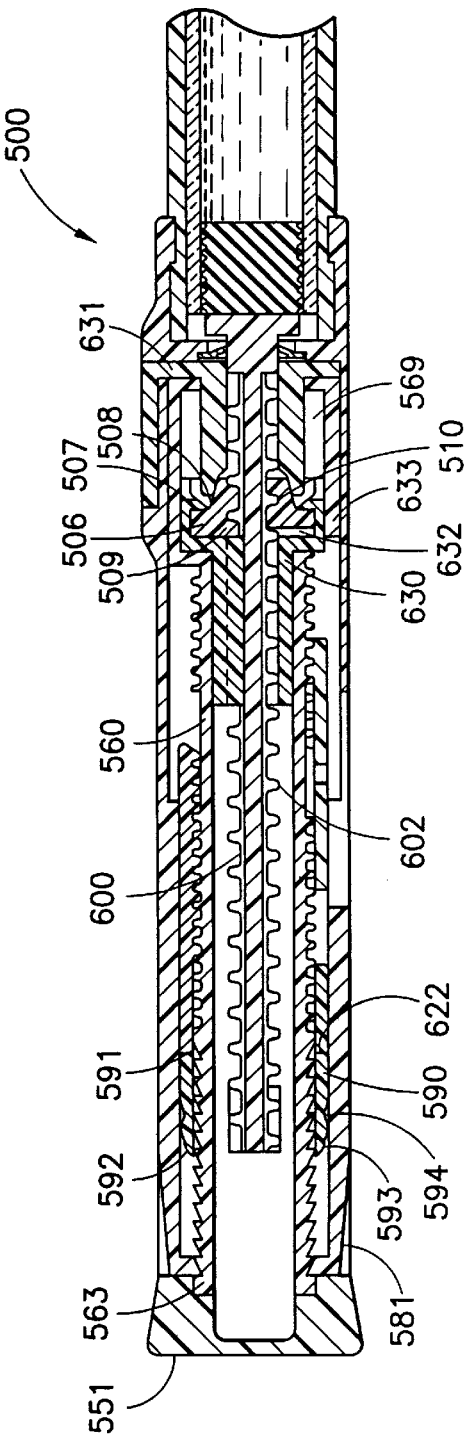
FIG. 16 is a cross-sectional view of the medication delivery pen shown in FIG. 15 in a dialing condition.

Ratchet nut housing 400 also includes a pair of anti-rotation keys 433 that work together with a pair of keyways (not shown) within dose window 370 to prevent ratchet nut housing 400 from rotating with respect to dose window 370, similarly to the earlier embodiments. In addition, dose window 370 also include a pair of anti-rotation keys (not shown) that are received in a pair of keyways 343 within housing 340 to prevent dose window 370 and ratchet nut housing 400 from rotating with respect to housing 340. Of course, ratchet nut housing 400 can move axially with respect to dose window 370 and both of these components can move axially with respect to housing 340. FIGS. 15–18 show various cross-sectional views of yet another embodiment of a repeat-dose medication delivery pen 500 10 according to the present invention. In particular, FIG. 15 shows medication delivery pen 500 in a ready for use condition, FIG. 16 shows the pen in a dialing condition, FIG. 17 shows the pen in an armed condition, and FIG. 18 shows the pen in an end of travel or dispense condition. All of these figures, of course, do not show the cap and pen-needle assembly which has been sufficiently described above with respect to the earlier embodiments. However, these figures do show a vial 530 having a vial system 539 all contained within a vial retainer 535.

As shown in FIG. 15, medication delivery pen 500 includes a housing 540 having a viewing port 541 through which an outer surface of dose window 570 is shown together with a viewing hole 571 extending through dose window 570. Through viewing hole 571 and viewing port 541 one of a plurality of dosage numerals (now shown) printed on a dose barrel 560, discussed below, is visible to a user. Of course, either viewing port 541 or viewing hole 570 may incorporate the magnifying lens to enlarge the dosage numerals to increase readability of these numerals. In addition, FIGS. 15–18 also show means for indicating whether medication delivery pen 500 is armed and ready for medication dispensing as well as indicating when medication has been properly dispensed as represented by a dosing pawl 581 that extends radial from an outer surface of housing 540. This configuration is slightly different from the earlier embodiment where the dosing pawl extending from a pawl housing or assembly.

FIGS. 15–18 show medication delivery pen 500 including a drive mechanism, a dosing control mechanism, and the above mentioned means for indicating whether medication delivery pen 500 is armed. The drive mechanism is comprised of a plunger 600, substantially similar to plunger 300 described in FIG. 11–14, have a shaft 604 having a plurality of threads 602 and a plunger face 601 at its distal end and a slot 603 extending from plunger face 601 to near a proximal end of said shaft 604.

Medication delivery pen 500 includes a housing 540 having a distal end 542 and a proximal end 549 including a plurality of dosing pawls 581 extending therefrom. It should be appreciated that in the current embodiment the earlier described pawl housing or assembly has been integrated onto the proximal end of housing 540. Medication delivery pen 500 also includes a dose knob 551 and a dose window 570 that are very similar to the embodiment described in FIGS. 11–14, but have some variations. In particular, dose barrel 560 now includes two sets of threads including a dose indicator thread 568 at a distal end 562 that engages matching threads 576 on the inside surface of dose window 570 and a dose setting thread 564 spaced from dose indicator threads 568 in a proximal direction and designed to meet with dose setting threads 621 on a stop sleeve 620, described further below. Dose barrel 560 also includes a set of dose ratchets 555 near a proximal end 563, but also includes a cylindrical cavity 569 within distal end 562. A dose knob 551 is fixed on proximal end 563 of dose barrel 560 and is used to rotate dose barrel 560 during dose setting, as shown in FIG. 16.

Housing 304 also includes a star washer 610 near its distal end 542 which perform the same function as an earlier embodiments. Medication delivery pen 500 also includes a sliding sleeve 590 have a distal surface 591 and a proximal surface 592 with a plurality of lateral grooves 593 and detents 594 on the outer surface of sliding sleeve 590. Medication delivery pen 500 also includes a stop sleeve 620 having dose setting threads 621 therein and a proximal face 622 that is used to push on distal face 591 of sliding sleeve 590 as medication delivery pen 500 is moved into the armed condition, as performed by shoulder 367 on dose barrel 360 in the previous embodiment. Dose setting threads 621 within stop sleeve 620 interact with dose setting thread 564 on dose barrel 560 in similar matter as threads 376 within dose window 370 interacted with threads 364 on dose barrel 360 in the earlier embodiment. In the current embodiment this feature has been separated from dose window 570 so to separate the function of the dose displaying means from dose setting means which allow more variability and functionality to be added to the dose setting display means.

In medication delivery pen 500 ratchet nut 406 and ratchet nut housing 400 have been replaced with a plunger nut 506 and an inner housing 630. Plunger nut 506 includes inner threads 510 that threadably meet with threads 602 on plunger 600 and also includes a proximal end ratchet 509 and a distal end ratchet 508 with a shoulder 507 facing in a distal direction and located therebetween. Inner housing 630 is received in cylindrical cavity 569 of dose barrel 560 and includes an open distal end 631 having an inner ratchet shoulder 632 that receives plunger nut 506 such that ratchet shoulder 632 interfaces with proximal end ratchet 509 on plunger nut 506 to allow rotation of plunger nut 506 during arming of medication delivery pen 500, but prevents rotation of plunger nut 506 in the other direction during movement of medication delivery pen 500 from the armed position to the fully dispensed position. Inner housing 630 also includes a plurality of spring fingers 633 extending radial from the inner surface of inner housing 630 to interface with shoulder 507 on plunger nut 506 to retain plunger nut 506 within inner housing 630.

Medication delivery pen 500 also includes a priming control mechanism like that described in the earlier embodiment which is rotatably mounted on housing 540 to allow a user to prime medication delivery pen 500 prior to arming the medication delivery pen 500. Priming control mechanism 700 includes an inner sleeve 701 and an outer sleeve 702 having a textured surface to aide the user in rotating priming control 700. Inner sleeve 701 include priming control ratchet 703 at a proximal end 704 that meets with distal end ratchet 508 on plunger nut 506 so that rotation of priming control mechanism 700 causes rotation of plunger nut 506 that then causes movement of plunger 600 in a distal direction to dispense medication from medication delivery pen 500 during a priming operation. Priming control mechanism 700 and its priming control ratchet 703 are designed so that they only provide rotational forces to plunger nut 506 in one direction. Of course, inner and outer sleeves 701 and 702 are merely exemplary and are not required to be fully closed sleeves and ratchets 703 and 508, commonly referred to as a "dog-face clutch," could be replaced with a ratchet and pawl interface like that used in the earlier embodiment.

While the present invention has been described with respect to a preferred embodiment and numerous alternative embodiments, it is apparent that various changes can be made to these embodiments without departing from the scope of the invention as defined by the appended claims.

What is claimed is:

1. A medication delivery pen comprising:

a pen-needle assembly;

a vial retainer including a vial containing a medication to be delivered and having said pen-needle assembly removably attached to a distal end;

a housing having said vial retainer mounted to a distal end and including;

a dose control mechanism extending from said housing for setting a desired dose to be delivered from the vial;

a drive mechanism is within said housing for dispensing the desired dose from the vial when in an armed condition, said drive mechanism including a plunger having a plunger face and a proximal shaft extending within said housing in a direction from said plunger face and means for driving said plunger in the distal direction when medication is to be dispensed from the vial; and means for priming said pen-needle assembly including a priming pawl that interfaces with said means for driving said plunger to cause said plunger to move in the distal direction.

2. A medication delivery pen according to claim 1, wherein said priming means is separate from said dose control mechanism.

3. A medication delivery pen according to claim 1, further comprising means for repeating the desired dose.

4. A medication delivery pen comprising:

a pen-needle assembly;

a vial retainer including a vial containing a medication to be delivered and having said pen-needle assembly removably attached to a distal end;

a housing having said vial retainer mounted to a distal end and including;

extending from said housing for setting a desired dose to be delivered from the vial;

a drive mechanism with said housing for dispensing the desired dose from the vial when in an armed condition, said drive mechanism including a plunger having a plunger face and a proximal shaft extending within said housing in a direction from said plunger face and means for driving said plunger in the distal direction when medication is to be dispensed from the vial; and means for priming said pen-needle assembly including a ratchet that interfaces with said means for driving said plunger to cause said plunger to move in the distal direction.

5. A medication delivery pen according to claim 4, wherein said priming means is separate from said dose control mechanism.

6. A medication delivery pen according to claim 4, further comprising means for repeating the desired dose.

7. A medication delivery pen comprising:

a pen-needle assembly;

a vial retainer including a vial containing a medication to be delivered and having said pen-needle assembly removably attached to a distal end;

a housing having said vial retainer mounted to a distal end and including;

a dose control mechanism extending from said housing for setting a desired dose to be delivered from the vial;

a drive mechanism within said housing for dispensing the desired dose from the vial when in an armed condition, said drive mechanism including a plunger having a plunger face and a shaft extending within said housing in a proximal direction from said plunger face and means for driving said plunger in the distal direction when medication is to be dispensed from the vial; and means for priming said pen-needle assembly, wherein said driving means includes a nut that travels on said shaft of said plunger and drives said plunger in the distal direction when medication is to be dispensed from the vial, and wherein said priming means includes a priming control sleeve mounted on said housing having a priming pawl that interfaces with said nut for driving said plunger in the distal direction.

8. A medication delivery pen according to claim 7, wherein said priming means is separate from said dose control mechanism.

9. A medication delivery pen according to claim 7, further comprising means for repeating the desired dose.

10. A medication delivery pen comprising:

a pen-needle assembly;

a vial retainer including a vial containing a medication to be delivered and having said pen-needle assembly removably attached to a distal end;

a housing having said vial retainer mounted to a distal end and including;

a dose control mechanism extending from said housing for setting a desired dose to be delivered for the vial;

a drive mechanism within said housing for dispensing the desired dose from the vial when in an armed condition, said drive mechanism including a plunger having a plunger face and a shaft extending within said housing in a proximal direction from said plunger face and means for driving said plunger in the distal direction when medication is to be dispensed from the vial; and means for priming said pen-needle assembly, wherein said driving means includes a nut that travels on said shaft of said plunger and drives said plunger in the distal direction when medication is to be dispensed from the vial, and wherein said priming means includes a priming control sleeve mounted on said housing having a ratchet that interferes with said nut for driving said plunger in the distal direction.

11. A medication delivery pen according to claim 10, wherein said priming means is separate from said dose control mechanism.

12. A medication delivery pen according to claim 10, further comprising means for repeating the desired dose.

* * * * *